(12) United States Patent
Jang et al.

(10) Patent No.: US 8,761,485 B2
(45) Date of Patent: Jun. 24, 2014

(54) METHOD AND SYSTEM OF PROCESSING MULTI-ENERGY X-RAY IMAGES

(75) Inventors: Kwang Eun Jang, Busan (KR); Dong Goo Kang, Suwon-si (KR); Young Hun Sung, Hwaseong-si (KR); Jong Ha Lee, Gyeonggi-do (KR); Sung Su Kim, Yongin-si (KR); Seok Min Han, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 359 days.

(21) Appl. No.: 12/929,173

(22) Filed: Jan. 5, 2011

(65) Prior Publication Data

US 2011/0164797 A1    Jul. 7, 2011

(30) Foreign Application Priority Data

Jan. 6, 2010    (KR) .................. 10-2010-0000801

(51) Int. Cl.
*G06K 9/00*    (2006.01)

(52) U.S. Cl.
USPC ........... 382/132; 382/128; 382/131; 382/254; 378/4; 378/5; 378/98.9; 378/53; 378/57; 600/425

(58) Field of Classification Search
None
See application file for complete search history.

(56) References Cited

U.S. PATENT DOCUMENTS

| | | | |
|---|---|---|---|
| 4,445,226 A | 4/1984 | Brody | |
| 4,939,760 A | 7/1990 | Kawai | |
| 5,827,187 A | 10/1998 | Wang et al. | |
| 7,583,779 B2 | 9/2009 | Tkaczyk et al. | |
| 7,627,078 B2 * | 12/2009 | Hsieh et al. | 378/4 |
| 7,778,454 B2 * | 8/2010 | Grasruck et al. | 382/128 |
| 7,876,874 B2 | 1/2011 | Goto et al. | |
| 7,920,735 B2 | 4/2011 | Krauss et al. | |
| 7,983,383 B2 | 7/2011 | Kadomura et al. | |
| 2003/0156684 A1 | 8/2003 | Fessler | |
| 2004/0092814 A1 * | 5/2004 | Hsieh et al. | 600/425 |
| 2004/0101088 A1 * | 5/2004 | Sabol et al. | 378/4 |
| 2004/0101090 A1 * | 5/2004 | Drummond et al. | 378/4 |
| 2004/0264628 A1 * | 12/2004 | Besson | 378/5 |
| 2005/0105687 A1 | 5/2005 | Heismann et al. | |
| 2006/0067460 A1 | 3/2006 | Price et al. | |

(Continued)

FOREIGN PATENT DOCUMENTS

| | | |
|---|---|---|
| CN | 1517071 A | 8/2004 |
| CN | 101023872 A | 8/2007 |

(Continued)

OTHER PUBLICATIONS

International Search Report issued on Sep. 19, 2011 for corresponding PCT Patent Application No. PCT/KR2011/000063.

(Continued)

*Primary Examiner* — Matthew Bella
*Assistant Examiner* — Jason Heidemann
(74) *Attorney, Agent, or Firm* — Staas & Halsey LLP

(57) ABSTRACT

Provided is a method and system of processing a multi-energy X-ray image. Through the method and system, a plurality of target images may be acquired using an X-ray detector enabling an energy separation to be performed in a predetermined time interval, with respect to a target where a contrast agent is applied, and a signal processing may be performed on the acquired target images, thereby detecting and reading benign/malignant lesions or masses.

26 Claims, 3 Drawing Sheets

(56) References Cited

U.S. PATENT DOCUMENTS

| | | | |
|---|---|---|---|
| 2006/0072799 A1 | 4/2006 | McLain | |
| 2006/0110018 A1 | 5/2006 | Chen et al. | |
| 2006/0251209 A1 | 11/2006 | Tkaczyk et al. | |
| 2007/0036418 A1* | 2/2007 | Pan et al. | 382/131 |
| 2007/0127789 A1* | 6/2007 | Hoppel et al. | 382/128 |
| 2007/0160276 A1 | 7/2007 | Chen et al. | |
| 2007/0195931 A1* | 8/2007 | Ohishi | 378/98.2 |
| 2007/0217570 A1* | 9/2007 | Grasruck et al. | 378/53 |
| 2007/0269013 A1 | 11/2007 | Liu et al. | |
| 2008/0013672 A1* | 1/2008 | Krauss et al. | 378/4 |
| 2009/0080740 A1 | 3/2009 | Shinagawa et al. | |
| 2009/0129538 A1 | 5/2009 | Tkaczyk et al. | |
| 2009/0147919 A1* | 6/2009 | Goto et al. | 378/86 |
| 2010/0014628 A1* | 1/2010 | Kadomura et al. | 378/4 |
| 2010/0135565 A1* | 6/2010 | Thomsen et al. | 382/132 |

FOREIGN PATENT DOCUMENTS

| | | |
|---|---|---|
| JP | 64-048209 | 2/1989 |
| JP | 2007-044275 | 2/2007 |
| JP | 2007-268273 | 10/2007 |
| WO | WO 2008/075595 | 6/2008 |

OTHER PUBLICATIONS

Written Opinion of the International searching Authority issued on Sep. 19, 2011 for corresponding PCT Patent Application No. PCT/KR2011/000063.

Kwang Eun Jang et al., "A Novel Material Decomposition Algorithm for Multienergy X-Ray Radiography Systems", Biomedical Imaging: From Nano to Macro, 2010 IEEE International Symposium on, IEEE, Apr. 14, 2010, pp. 800-803.

Extended European Search Report mailed Nov. 21, 2013 in related European Application No. 11731911.1.

Chinese Office Action dated Apr. 28, 2014 issued in corresponding Chinese Application No. 201180005598.8.

* cited by examiner

METHOD AND SYSTEM OF PROCESSING MULTI-ENERGY X-RAY IMAGES

CROSS-REFERENCE TO RELATED APPLICATIONS

This application claims the benefit of Korean Patent Application No. 10-2010-0000801, filed on Jan. 6, 2010, in the Korean Intellectual Property Office, the disclosure of which is incorporated herein by reference.

BACKGROUND

1. Field

One or more embodiments are directed a method and system of processing a multi-energy X-ray image.

2. Description of the Related Art

A system of processing a multi-energy X-ray image may acquire an X-ray image having at least two energy bands. In general, since differing materials are respectively seen as having unique X-ray attenuation characteristics in different energy bands, a separation of images for each material may be performed using the X-ray attenuation characteristics.

X-rays are widely used to detect masses that may represent cancer, while a system having high sensitivity may be required to make the determination of whether the mass is malignant. However, in an actual clinical diagnosis, such a high specificity in combination with high sensitivity is not available. Typically, such specificity is only obtained by an invasive biopsy to distinguish between a benign lesion or mass and a malignant lesion or mass, which may have substantial impact on patients. Thus, when it is difficult to distinguish between the benign lesion or mass and the malignant lesion or mass through current X-ray examinations, an invasive biopsy that excises a tissue from a suspicious area for examination may be required. Accordingly, detecting the malignant lesion or mass in human tissues through a non-invasive way using only X-ray image processing may be more desirable.

Recently, a cancer diagnosis performed using an X-ray image processing system is primarily conducted based on the detected shape of a mass, such as of a lesion. Since benign lesions or masses do not invade surrounding tissues, boundaries with surrounding tissues are likely to be smooth and rounded-shaped. Conversely, in a case of the malignant lesion or mass, the boundaries with surrounding tissues may be observed to be rough or non-smooth. Occasionally, a lesion or mass having the rounded shape may also turn out to be the malignant lesion or mass.

In general X-ray image processing is defined herein as being different from a three-dimensional (3D) X-ray Computed Tomography (CT) image processing, as the X-ray imaging processing bases observations on X-ray images where all pieces of depth direction data are overlapped. The three-dimensional (3D) X-ray Computed Tomography (CT) image processing would provide separate images for separate depths. Accordingly, when such a depth overlapping X-Ray imaging processing is used to detect whether a lesion or mass is benign or malignant, the boundary of the benign/malignant lesion tumor may be inaccurately identified due to other overlapping tissues that are different from the tissue of the examined lesion or mass and which may merely be at a different depth from the mass, e.g., either above or below.

In addition, an X-ray system can obtain images more quickly than the three-dimensional (3D) X-ray Computed Tomography (CT) image processing and thus, dynamics between images may be more easily observed with an X-ray system. Accordingly, the present inventors have found that there is a demand for a new X-ray image processing approach having both a high sensitivity and a high specificity, without the costs and time drawbacks of current systems.

SUMMARY

According to one or more embodiments, there is provided a method of processing a multi-energy X-ray image, the method including acquiring, in a predetermined time interval, a plurality of target images for each of at least two energy bands formed by a multi-energy X-ray after passing through a target where a contrast agent is applied, from a multi-energy X-ray source, and performing an image signal processing on the plurality of target images.

According to one or more embodiments, there is provided a method of using a multi-energy X-ray source to generate detected information from at least two energy bands of a multi-energy X-ray for generating a decomposition image of at least a select material of a target while the select material is within a body, the method including acquiring, in a predetermined time interval, a plurality of target images for each of the at least two energy bands formed by the multi-energy X-ray of the multi-energy X-ray source after passing through the target, and performing an image signal processing on the plurality of target images.

According to one or more embodiments, there is provided a method of processing a multi-energy X-ray image, the method including acquiring, in a predetermined time interval, a plurality of target images formed for each of at least two energy bands from a multi-energy X-ray passing through a target where a contrast agent is applied, from a multi-energy X-ray source, performing an image signal processing on the plurality of target images, including at least one of: processing an image from the plurality of target images for at least one of plural predetermined times within the predetermined time interval, and for each of the at least two energy bands of the multi-energy X-ray irradiated from the multi-energy X-ray source, performing a dynamics analysis of a measured amount of the contrast agent within the predetermined time interval, and measuring the amount of the contrast agent applied to the target by analyzing a material decomposition image from the target images for at least one material, with the at least one material at least including the contrast agent, and controlling the target image, resulting from the image signal processing, to be displayed through a display.

According to one or more embodiments, there is provided an apparatus for processing a multi-energy X-ray image, the apparatus including a control unit to control a multi-energy X-ray source to cause a multi-energy X-ray to be irradiated to a target during a predetermined time interval, an X-ray detector to acquire a plurality of target images for each of at least two energy bands of the multi-energy X-ray passing through the target where a contrast agent is applied, and an image processing and analyzing unit to perform an image signal processing on the plurality of target images, with the image signal processing including at least one of: processing an image for at least one of plural predetermined times within the predetermined time interval, and for each of the at least two energy bands of the multi-energy X-ray, performing a dynamics analysis of a measured amount of the contrast agent within the predetermined time interval, and measuring the amount of the contrast agent applied to the target by analyzing a material decomposition image from the target images for at least one, with the at least one material at least including the contrast agent.

Additional aspects, features, and/or advantages of embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of one or more embodiments, taken in conjunction with the accompanying drawings of which.

DETAILED DESCRIPTION

Figure 1:
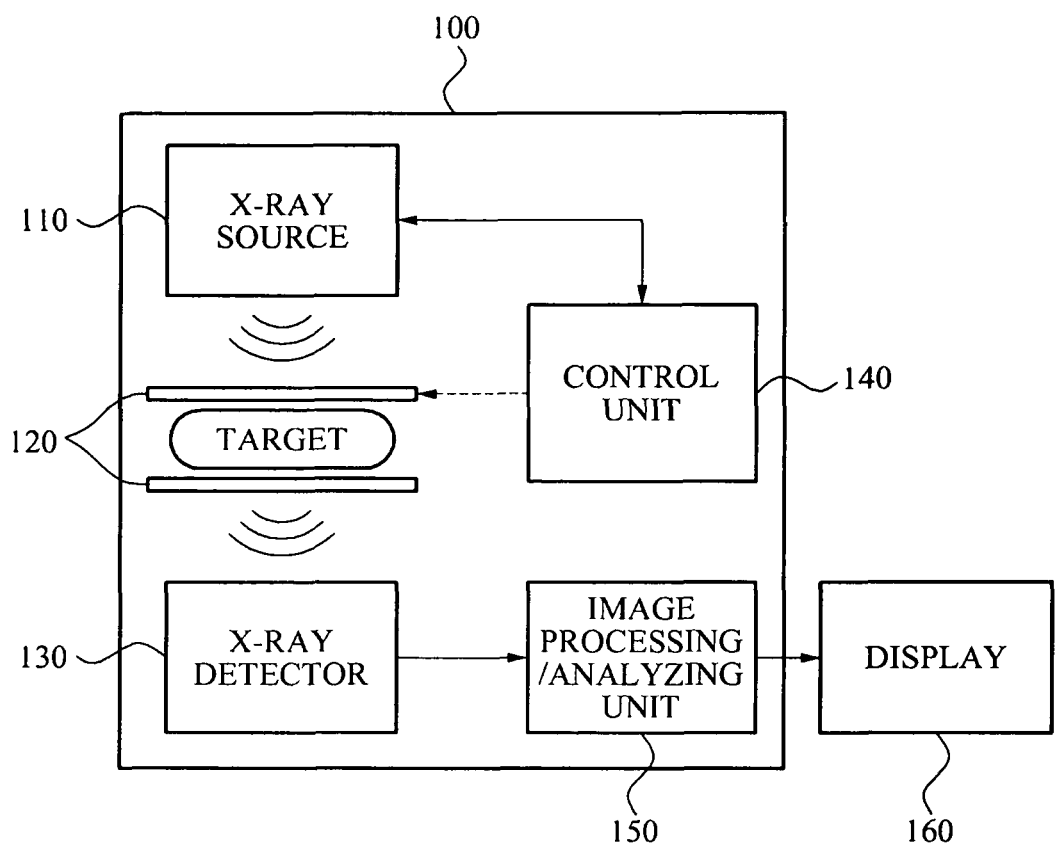
FIG. 1 illustrates a system of processing a multi-energy X-ray image, according to one or more embodiments.

Reference will now be made in detail to embodiments, examples of which are illustrated in the accompanying drawings, wherein like reference numerals refer to like elements throughout. In this regard, embodiments of the present invention may be embodied in many different forms and should not be construed as being limited to embodiments set forth herein. Accordingly, embodiments are merely described below, by referring to the figures, to explain aspects of the present invention.

In one or more embodiments, the system of processing a multi-energy X-ray image may include an X-ray detector configured to have the capability to perform a separation of images for each of two energy bands or more, and may further include any of a radiography system, a tomosynthesis system, a Computed Tomography (CT) system, and a nondestructive inspection that are also configured to have the capability to perform a separation of image for each of the two energy bands or more. These discussed systems are set forth merely as an example, and additional and/or alternate systems are equally available. Based on the disclosure herein, it should be well understood that the system of processing the multi-energy X-ray may be implemented for various intentions and cases, according to differing embodiments.

FIG. 1 illustrates a system 100 to process a multi-energy X-ray image, according to one or more embodiments.

Referring to FIG. 1, as only an example, the system 100 includes an X-ray detector 130, a control unit 140, and an image processing/analyzing unit 150. The system 100 may further include an X-ray source 110 and a stage 120 depending on implementation of the system 100.

The X-ray source 110 may radiate X-rays to a target illustrated in FIG. 1, noting that plural detectors are equally available in differing embodiments. The X-ray radiated from the X-ray source 110 may include photons having a plurality of energy levels, i.e., photons corresponding to different energy bands. The X-rays passing through the target may be detected by the X-ray detector 130. A dose/voltage of the X-rays radiated from the X-ray source 110 and a radiation time may be controlled by the control unit 140 which will be described in greater detail later.

The stage 120 may be a device that can fix the target. Depending on embodiments, the stage 120 may be designed to immobilize the target by applying a predetermined quantity of pressure to the target, or may remove the applied pressure from the target. In one or more embodiments, the illustrated stage includes a contrast administering device or system that provides a contrast to the target. The contrast administration may be performed in various manners so the contrast is sufficiently detectable in the desired location of the target, e.g., so it may be detected whether a lesion or mass at this location is benign or malignant. In this regard, briefly, it is further noted that according to Nature Medicine (Vol. 3, 780-782) published in 1997, a malignant lesion or mass may relatively rapidly absorb a contrast agent and may relatively rapidly wash-out the contrast agent compared with a normal tissue, for its physiological features. According, in one or more embodiments, the rapidity of absorption and rapidity of the wash-out can be measured and compared to known absorption rates and wash-out rates for both whether an examined lesion or mass is benign or malignant, but also for a characterization of the lesion or mass, e.g., with different types or stages or progression for malignancies having differing absorption and wash-out rates. As only an example, such rates and/or characterizations may be stored in a look up table memory of the image processing/analyzing unit 150, according to one or more embodiments.

A scheme of measuring dynamics of the contrast may be referred to as a dynamic contrast-enhanced imaging (DCE imaging) scheme, and is currently performed using magnetic resonance imaging (MRI). However, currently there is no X-ray system that is capable of applying such a DCE imaging scheme, or a corresponding detector for the same. However, an MRI system may be 30 times more expensive than an X-ray imaging processing system, and there is further greater delay in the generating of images with the MRI system than with the X-ray imaging processing system. Thus, dynamic measurement by MRI systems are both extremely expensive and require greater time to perform such a measurement, resulting in less examinations and more patient time and costs for each examination, and less availability of testing centers that can afford the more costly MRI systems or their use.

Accordingly, the X-ray detector 130 may acquire a plurality of target images formed by passing multi-energy X-rays through a target where a contrast agent is applied, from a multi-energy X-ray source 110. More specifically, the X-ray detector 130 may detect an X-ray photon entering from the X-ray source 110 for each of plural energy bands, thereby acquiring the plurality of target images generated by the detected photons passing through the target. In one or more embodiments, the X-ray detector 130 may alternatively or in addition detect an X-ray photon entering from the X-ray source 110 for each of plural energy levels. In on or more embodiments, the X-ray detector 130 may be a photo counting detector (PCD) that is currently being developed, which may discriminate between energy bands/levels, and may provide relatively excellent signal to noise ratio (SNR) with respect to a small amount of X-ray.

The control unit 140 may control the X-ray source 110 to enable the multi-energy X-rays to be radiated to the target in a predetermined dose/voltage within or during a predetermined time interval. In addition, at any point during the process the control unit 140 may control the stage 120 to adjust the pressure applied to the target. Greater pressure or support may be applied selectively during such a predetermined time interval, and/or pressure or support may be reduced outside of the predetermined time interval, as only an example.

The image processing/analyzing unit 150 may perform image processing on the target images acquired during the predetermined period of time. In one or more embodiments, the image processing performed in the image processing/analyzing unit 150 may include at least one of the following five schemes, as only examples, noting that alternative are also available.

(1) Pre-Processing Scheme for Target Image

In this example, multi-energy data may be read for each time interval, and a pre-processing may then be performed. The pre-processing may include a basic image pre-processing.

As another example of the pre-processing, a Region of Interest (ROI) desired to be detected from the target may be determined before the target image is generated, and surrounding target images of the detected ROI may be separately stored, so that the stored target images may be differently referred to as an image of the target image and potentially separately displayed. Another example of the pre-processing is a removal, from a target image, of a motion artifact generated due to a detected or determined movement of the target or body while monitoring the target body area or one or more other body areas.

(2) Processing and Synthesis Scheme for Target Image

In this example, the plurality of target images acquired using the X-ray detector 130 may be separated into respective images for at least one of each predetermined time(s) within the predetermined time interval, and for plural energy bands. A weighted sum scheme may be applied to a corresponding image to process and synthesize the target images.

(3) Material Decomposition Scheme for Target Image

In one or more embodiments, a material decomposition scheme may be performed by applying a material decomposition algorithm to the target image. The material decomposition algorithm provides a process for decomposing information of photon data, for example, into separately displayable components or materials, such as through an image representing a sought material in the target images, e.g., the contrast or other known materials, as well as an image representing a photoelectric attenuation of the X-rayed area of the body including the target, an image representing a Compton scatter of the area, an image representing a subtraction image for at least the predetermined time interval corresponding to respective target images of at least two energy bands, and an image representing angiography or arteriography, according to one or more embodiments. These separately defined components each can separately show information for one or more desired materials. For example, if the contrast medium is iodine, then the material may be iodine, and the overall detected X-ray information may be decomposed to primarily show information for iodine. As noted above, as only an example, as malignant lesions or masses may more readily absorb the particular contrast medium, and rapidly wash out the contrast medium, if the images detected by X-ray detector 130 were decomposed to show primarily the contrast medium then it may be determined whether a targeted lesion or mass is more likely or less likely to be malignant within a predetermined time interval. The decomposition based upon material may also be able to classify such lesions or masses according to their composition, in addition to a determination of whether a lesion or mass is benign or malignant.

Thus, as an example of the material decomposition scheme, respective projection images (E1 through EN) of energy bands generated by passing a multi-energy X-ray spectrum through a target constituting at least one material are received, and an initial image is estimated for each of M materials that may be constituting the target. As only an example, the at least one material may at least be the contrast medium. Each of the M materials would represent a different 'material' that may be selectively decomposed from the detected X-rays that have passed through the target.

Subsequently, in the material decomposition scheme, the system 100 is simulated based on an initial image. The simulated system 100 may be represented as the following Equation 1, for example.

$$Y_3(r) \int_{E_{s_1}}^{E_{r_2}} I_3(E) \exp(-F_j(x(r), E)) dE + n_j(r) \quad \text{Equation 1}$$

Here Y denotes a measurement image of the system 100 measured in a j-th energy band, and I denotes a function obtained based on an effect of the X-ray source 110 radiated to a target and based on a response effect of the X-ray detector 130 and a known function signifying spectrum information of the system 100. F denotes a function of (x and E) obtained based on a component ratio of the materials constituting the target in a corresponding energy band, j denotes an index of an energy band, and r denotes a location vector (e.g. (x, y) in a 2D image, and (x, y, z) in a 3D image) of an N-dimension. E denotes an energy variable, and n denotes a noise term. Since an X-ray attenuation characteristic is changed based on a material existing in 'r' of a target, an internal structure of the target may be expressed in the X-ray image. However, when integrating all energy bands, a difference of inter-material attenuation characteristic may be reduced, so that it may be difficult to express the internal structure of the target. Accordingly, in the system of processing the multi energy X-ray image, as illustrated in Equation 1, the plurality of target images may be acquired by dividing, by N, an integration interval ranging from zero to infinity.

As illustrated in Equation 1, x(r) is obtained by the function Y of the simulated system 100, and an optimal x(r) may be obtained through an iteration operation performed a predetermined number of times.

As one of the methods of acquiring x(r) by simulating the system 100 using the function Y, a fidelity term may be configured. The fidelity term may denote a term that may express similarity with a measurement value of the system 100, according to one or more embodiments. For convenience of description, a Poisson Log-Likelihood function may be used as the fidelity term. An Iterative Coordinate Descent with Newton-Raphson (ICD/NR) scheme that may adopt an NR updating scheme using Poisson Log-Likelihood similarity and identity for Kullback-Leibler (KL) divergence may also be applied, noting that alternative schemes are also available.

For example, in Equation 1, assuming that $$F_j(x, E) = \sum_i \mu_i(E_k) L_i$$

and a vector type is $$\frac{1}{2}(L - \hat{L})^T A(L - \hat{L}) - b^T L,$$

the fidelity term may be expressed as the following Equation 2, for example.

$$A = \sum_k \left( \mu(E_k)\mu^T(E_k) \left( \sum_j I_j(E_k)\exp\left(-\sum_i \mu_i(E_k)\hat{L}_i\right) \right) \right), \quad \text{Equation 2}$$

and $$b = \sum_j (1-w_j) \cdot \left( \sum_k I_j(E_k)\exp\left(-\sum_i \mu_i(E_k)\hat{L}_i\right) \mu(E_k) \right)$$

Here:

$$w_j = \frac{Y_j}{\sum_k I_j(E_k)\exp\left(-\sum_i \mu_i(E_k)\hat{L}_i\right)}$$

In Equation 2, $\mu_i(E_k)$ denotes an attenuation characteristic curve based on an energy of an i-th material of a k-th updating procedure, and $L_i$ denotes an amount (length) of the i-th material. A function F defined in Equation 2 may be merely an example used for convenience of description, and may be defined differently in one or more embodiments depending on implementation of the system 100.

As described above, the fidelity term may be configured, and an optimized function may be determined using the configured fidelity team. The determination of the optimized function may be performed such that a correction value minimizing a predetermined cost function using the fidelity term is determined, and the initial image is updated to a material decomposition image by applying the correction value to the initial image. Here, the determination of the optimized function may be performed in one of a pixel unit, a block unit, and an image unit, as only examples.

According one or more embodiments, a predetermined regularization term may be further included in the fidelity term configured as illustrated in Equation 2 to thereby determine the optimized function.

When a quadratic regularization term is used as an example of the regularization term, the optimized function may be determined using an equation of (A+R)x=b, for example. When using a regularization term different from the quadratic regularization term, the optimized function may be mathematically determined. When using the quadratic regularization term, instead of using the matrix A of Equation 2 the following Equation 3, for example, may be used.

$$A' = A + \gamma R \quad \text{Equation 3}$$

In Equation 3, a measurement value obtained by measuring an amount of a material updated with respect to a given $L_i$ using an inverse matrix operation method may be obtained.

As described above, the material decomposition image may be generated by updating the initial image, and then the iteration operation may be performed the predetermined number of times, e.g., within the predetermined interval. The material decomposition image having superior quality may be obtained through the iteration operation.

Through the material decomposition image obtained in the above described process, an amount of a contrast agent applied to a target may be measured.

(4) Dynamics Analysis Scheme

In one or more embodiment, the amount of the contrast agent may be quantitatively measured by adopting such an above described material decomposition algorithm, and dynamics for a contrast of masses of benign/malignant lesions of a target may be quantitatively measured based on the measured amount of the contrast agent. Dynamics for a contrast for alternative masses of a target may also be quantitatively measured based on the measured amount of the contrast agent. Since the benign/malignant lesions or masses show mutually different dynamics distributions, as noted above, the system 100 may be used as a diagnosis device by utilizing the dynamics analysis scheme, thereby improving specificity of the benign/malignant lesions or masses.

(5) Post-Processing Scheme

In one or more embodiments, a post-processing scheme may be performed on the target image obtained by being subjected to at least one of the above described image processing schemes (1) to (4). As examples of a post-processing scheme, an image processing scheme used for convenience of a user and a computer-aided-diagnosis (CAD) processing scheme may be given, noting that alternatives are also available.

The system 100 may perform the image processing in various combinations of the above described image processing schemes (1) to (5), for example. According to an embodiment, the pre-processing scheme (1) and the post-processing scheme (5) may be selectively used. For example, only the processing and synthesis scheme (2) may be adopted, and only the material decomposition scheme (3) may be adopted. Alternatively, both the material decomposition scheme (3) and the dynamics analysis scheme (4) may be adopted. This will be described in greater detail with reference to FIG. 3.

The target image having been processed by the image processing/analyzing unit 150 may be displayed through a predetermined display 160, such as that shown in FIG. 1.

Figure 2:
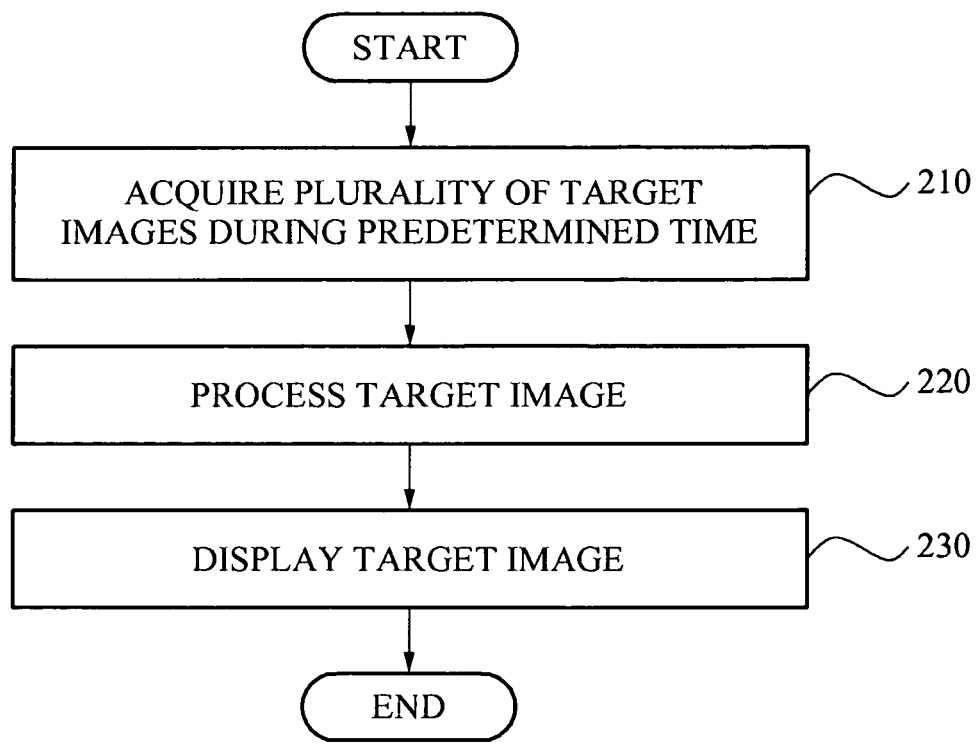
FIG. 2 illustrates a method of processing a multi-energy X-ray image, according to one or more embodiments.

FIG. 2 is a flowchart illustrating a method of processing a multi-energy X-ray image, according to one or more embodiments.

In operation 210, according to one or more embodiments, a plurality of target images formed by passing a multi-energy X-ray through a target where a contrast agent is applied may be detected.

In operation 220, an image processing may be performed on the obtained plurality of target images. In operation 230, the processed target images may be stored and/or displayed through a display, such as that shown in FIG. 1. As only an example, the image processing performed in operation 220 will be described in greater detail with reference to FIG. 3.

Figure 3:
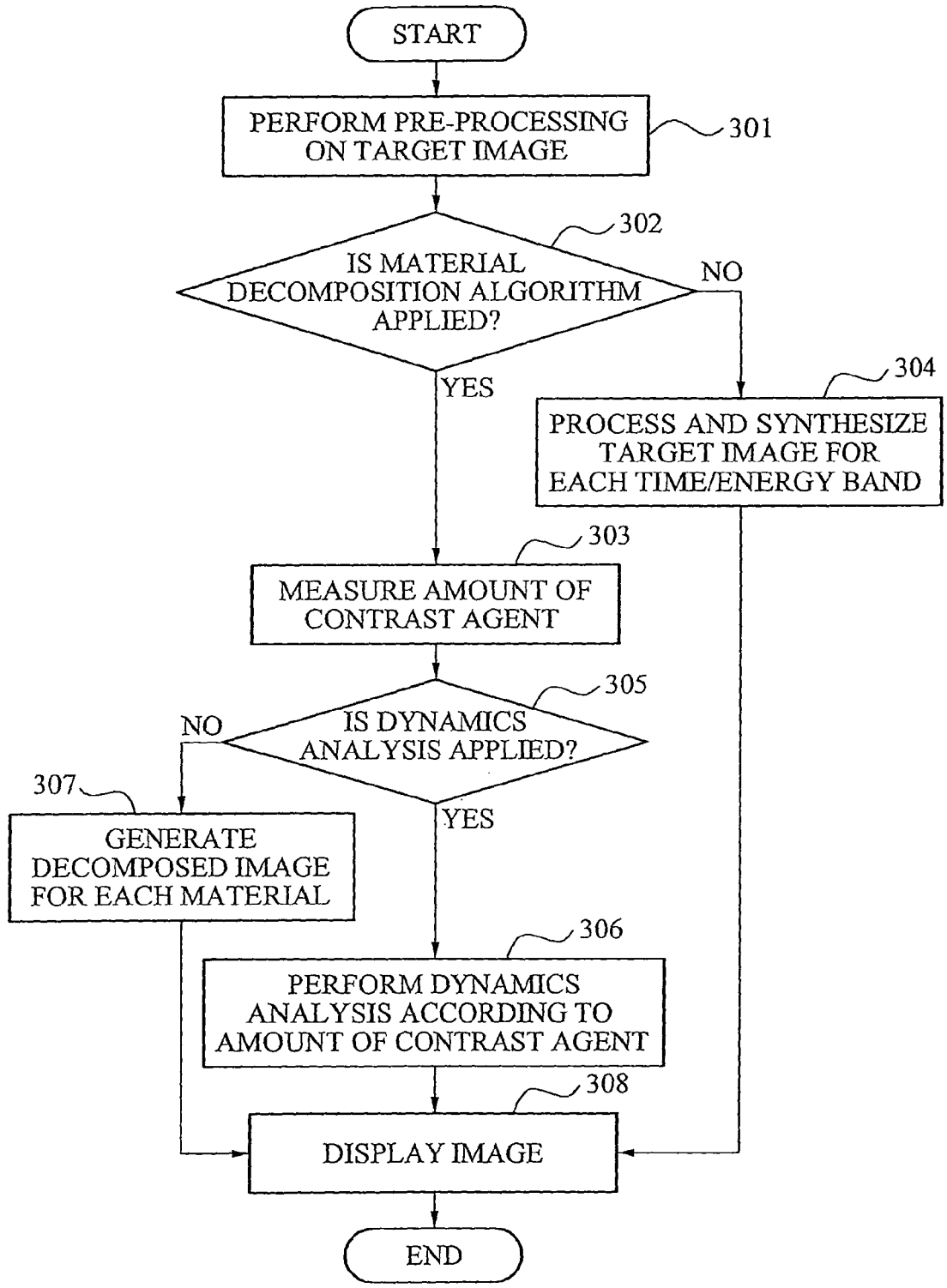
FIG. 3 illustrates an image processing method, according to one or more embodiments.

FIG. 3 illustrates an image processing method, according to one or more embodiments.

In operation 301, a pre-processing may be performed on a target image. As an example of the pre-processing, a Region of Interest (ROI) of the target desired to be detected may be predetermined, and target images surrounding the ROI may be separately stored. Another example of the pre-processing is the aforementioned removal, from a target image, of a motion artifact potentially generated due to a movement while measuring a human body, as only an example.

In operation 302, there is determination of whether a material decomposition algorithm is being applied to the pre-processed target image. In operation 303, when the material decomposition algorithm is applied to the pre-processed target image, the system may measure an amount of the contrast agent applied to the target by applying the material decomposition algorithm to the target image.

In operation 304, when the material decomposition algorithm is not applied to the pre-processed target image, the target image for each predetermined time and for each energy band may be processed and synthesized. In operation 304, the acquired plurality of target images may be divided into images for at least one of each predetermined time within a predetermined time interval and for each energy band, and corresponding images may be synthesized by adopting a weighted sum scheme, as only an example. In operation S308, the synthesized image may be stored and/or displayed through a display, such as the display of FIG. 1.

In operation 305, the amount of the contrast agent may be quantitatively measured, and then a determination may be made as to whether to adopt the dynamics analysis scheme, e.g., based on this quantitative measurement. In operation 306, when the dynamics analysis scheme is determined to be adopted in operation 305, the dynamics analysis of the measured amount of the contrast agent may be performed within the time interval. More specifically, dynamics for a contrast of masses of benign/malignant lesions of the target may be quantitatively measured based on the measured amount of the contrast, for example. In an embodiment, the measured dynamics are compared to a dynamics table, e.g., stored in the image processing/analyzing unit 150 of FIG. 1, which identifies whether the measured dynamics is indicative of a benign/malignant lesion or mass. In operation 308, the target image having the dynamics analysis performed may be stored in a memory, e.g., of the image processing/analyzing unit 150 of FIG. 1, and/or displayed through a display, such as that of FIG. 1. In an embodiment, the result of the comparison with the table for the lesion or mass is stored in the memory, and potentially also displayed through the display.

In operation 307, when the dynamics analysis scheme is determined to not be adopted in operation 305, a material decomposition image for each select material may be generated based on the measured amount of the contrast agent. In operation 308, the generated material decomposition image may be stored in the memory and/or displayed through the display.

Operation 307 may further include a post-processing performance on the target images before performing operation 308.

In the image processing method of FIG. 3, all or select operations 301 to 307 may be applied based on a user input or a system setting, for example, such as for performing differing tests. As described above with reference to FIG. 1, the image processing/synthesis may be performed on the target images for each predetermined time and for each energy band without adopting the material decomposition algorithm, based on the implementation of the system 100, or the image processing may be performed by adopting the material decomposition algorithm. Alternatively, the material decomposition algorithm may be adopted and then the dynamics analysis may be performed. These combinations of the image processing schemes may be provided in various manners, and the above should not be considered as limiting.

In one or more embodiments, apparatus, system, and unit descriptions herein include one or more hardware processing elements. For example, each described unit may include one or more processing elements performing the described operation, desirable memory, and any desired hardware input/output transmission devices. Further, the term apparatus should be considered synonymous with elements of a physical system, not limited to a single enclosure or all described elements embodied in single respective enclosures in all embodiments, but rather, depending on embodiment, is open to being embodied together or separately in differing enclosures and/or locations through differing hardware elements.

In addition to the above described embodiments, embodiments can also be implemented through computer readable code/instructions in/on a non-transitory medium, e.g., a computer readable medium, to control at least one processing device, such as a processor or computer, to implement any above described embodiment. The medium can correspond to any defined, measurable, and tangible structure permitting the storing and/or transmission of the computer readable code.

The media may also include, e.g., in combination with the computer readable code, data files, data structures, and the like. One or more embodiments of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Computer readable code may include both machine code, such as produced by a compiler, and files containing higher level code that may be executed by the computer using an interpreter, for example. The media may also be a distributed network, so that the computer readable code is stored and executed in a distributed fashion. Still further, as only an example, the processing element could include a processor or a computer processor, and processing elements may be distributed and/or included in a single device.

The computer-readable media may also be embodied in at least one application specific integrated circuit (ASIC) or Field Programmable Gate Array (FPGA), which executes (processes like a processor) program instructions.

While aspects of the present invention has been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. A method of processing a multi-energy X-ray image, the method comprising:
    acquiring, in a predetermined time interval, a plurality of target images for each of at least two energy bands formed by a multi-energy X-ray after passing through a target where a contrast agent is applied, from a multi-energy X-ray source; and
    performing an image signal processing on the plurality of target images, further comprising:
    estimating respective initial images for at least one of plural materials, over the predetermined time interval, using the plurality of target images;
    updating an initial estimated image of the estimated respective initial images based on, at least, one of later estimated images of the estimated respective initial images for the at least one of plural materials; and
    generating a material decomposition image based on the updating of the initial estimated image.
2. The method of claim 1, wherein the performing of the image signal processing includes for each energy band of the multi-energy X-ray irradiated from the multi-energy X-ray source, processing an image from the plurality of target images collected within the predetermined time interval.

3. The method of claim 1, further comprising performing a pre-processing on the plurality of target images including searching for a predetermined Region of Interest (ROI) within the plurality of target images, and separately storing a target image including the searched ROI from target images.

4. The method of claim 1, further comprising performing a pre-processing on the plurality of target images by removing from at least one target image a motion artifact.

5. The method of claim 1, wherein the performing of the image signal processing comprises decomposing information from the plurality of target images into separately displayable components or materials including at least one of an image representing photoelectric attenuation of a corresponding area of the body including the target, an image representing a Compton scatter of the area, an image representing a subtraction image for at least the predetermined time interval corresponding to respective target images of the at least two energy bands, and an image representing an X-ray angiography for the area.

6. At least one non-transitory medium comprising computer readable instructions to control at least one processing element to implement the method of claim 1.

7. A method of processing a multi-energy X-ray image, the method comprising:
acquiring, in a predetermined time interval, a plurality of target images for each of at least two energy bands formed by a multi-energy X-ray after passing through a target where a contrast agent is applied, from a multi-energy X-ray source; and
performing an image signal processing on the plurality of target images,
wherein the performing of the image signal processing comprises:
estimating respective initial images for each of plural materials, using the plurality of target images;
acquiring respective material decomposition images for each of the plural materials from the respective initial images, determining a correction value for minimizing a predetermined cost function, and
updating an initial image for one of the plural materials, of the respective initial images, to a material decomposition image based on predetermined material decomposition algorithm by applying the determined correction value to the initial image; and
measuring an amount of the contrast agent applied to the target by analyzing the material decomposition image when one of the plural materials is the contrast agent.

8. The method of claim 7, wherein the performing of the image signal processing further comprises:
performing a dynamics analysis of the amount of the contrast agent within the predetermined time interval.

9. At least one non-transitory medium comprising computer readable instructions to control at least one processing element to implement the method of claim 7.

10. A method of using a multi-energy X-ray source to generate detected information from at least two energy bands of a multi-energy X-ray for generating a decomposition image of at least a select material of a target while the select material is within a body, the method comprising:
acquiring, in a predetermined time interval, a plurality of target images for each of the at least two energy bands formed by the multi-energy X-ray of the multi-energy X-ray source after passing through the target; and
performing an image signal processing on the plurality of target images, further comprising:
estimating respective estimated images for at least one of plural materials, over the predetermined time interval, using the plurality of target images;
updating an initial estimated image of the estimated images based on, at least, one of later estimated images of the estimated images for the at least one of plural materials; and
generating a material decomposition image based on the updating of the initial estimated image.

11. The method of claim 10, further comprising administering a contrast agent to the body as the select material.

12. The method of claim 11, wherein the performing of the image signal processing comprises decomposing information from the plurality of target images into separately displayable components or materials including at least one of an image representing photoelectric attenuation of a corresponding area of the body including the target, an image representing a Compton scatter of the area, an image representing a subtraction image for at least the predetermined time interval corresponding to respective target images of the at least two energy bands, and an image representing an X-ray angiography for the area.

13. At least one non-transitory medium comprising computer readable instructions to control at least one processing element to implement the method of claim 10.

14. A method of using a multi-energy X-ray source to generate detected information from at least two energy bands of a multi-energy X-ray for generating a decomposition image of at least a select material of a target while the select material is within a body, the method comprising:
acquiring, in a predetermined time interval, a plurality of target images for each of the at least two energy bands formed by the multi-energy X-ray of the multi-energy X-ray source after passing through the target;
performing an image signal processing on the plurality of target images; and
administering a contrast agent to the body as the select material,
wherein the performing of the image signal processing comprises:
measuring an amount of the contrast agent found within the target based on the material decomposition image;
measuring dynamics over time of the amount of the contrast agent of the target within the predetermined time interval; and
diagnosing at least whether a lesion or mass within the target is malignant by comparing the measured dynamics with a dynamics table.

15. The method of claim 14, wherein a result of the comparison is output to a user.

16. A method of using a multi-energy X-ray source to generate detected information from at least two energy bands of a multi-energy X-ray for generating a decomposition image of at least a select material of a target while the select material is within a body, the method comprising:
acquiring, in a predetermined time interval, a plurality of target images for each of the at least two energy bands formed by the multi-energy X-ray of the multi-energy X-ray source after passing through the target; and
performing an image signal processing on the plurality of target images,
wherein the performing of the image signal processing comprises:
measuring an amount of the contrast agent, as the select material, found within the target based on the material decomposition image;

measuring dynamics over time of the amount of the contrast agent of the target within the predetermined time interval; and diagnosing at least whether a lesion or mass within the target is malignant by comparing the measured dynamics with a dynamics table.

17. The method of claim 16, wherein the decomposition image is updated plural
predetermined times within the predetermined time interval missing.

18. At least one non-transitory medium comprising computer readable instructions to control at least one processing element to implement the method of claim 16.

19. A method of processing a multi-energy X-ray image, the method comprising:
acquiring, in a predetermined time interval, a plurality of target images formed for each of at least two energy bands from a multi-energy X-ray passing through a target where a contrast is applied, from a multi-energy X-ray source;
performing an image signal processing on the plurality of target images, further comprising:
estimating respective initial images for at least one of plural materials, over the predetermined time interval, using the plurality of target images;
updating an initial estimated image of the estimated respective initial images based on, at least, one of later estimated images of the estimated respective initial images for the at least one of plural materials; and
generating a material decomposition image based on the updating of the initial estimated image,
wherein the performing of the image signal processing on the plurality of target images include at least one of:
processing the estimated respective initial images for the at least one of the plural materials, using the plurality of target images for plural predetermined times within the predetermined time interval, and for each of the at least two energy bands of the multi-energy X-ray irradiated from the multi-energy X-ray source,
performing a dynamics analysis of a measured amount of the contrast agent within the predetermined time interval,
measuring the amount of the contrast agent applied to the target by analyzing a material decomposition image, which is based on the updating of the initial estimated image, wherein the at least one of plural materials includes the contrast agent, and
controlling one of the target image and the material decomposition image, resulting from the image signal processing, to be displayed through a display.

20. The method of claim 19, wherein the performing of the image signal processing comprises decomposing information from the plurality of target images into separately displayable components or materials including at least one of an image representing photoelectric attenuation of a corresponding area of the body including the target, an image representing a Compton scatter of the area, an image representing a subtraction image for at least the predetermined time interval corresponding to respective target images of the at least two energy bands, and an image representing an X-ray angiography for the area.

21. The method of claim 19, further comprising comparing the measured dynamics with a dynamics table to diagnose whether a lesion or mass within the target is malignant.

22. At least one non-transitory medium comprising computer readable instructions to control at least one processing element to implement the method of claim 19.

23. An apparatus for processing a multi-energy X-ray image, the apparatus comprising:
a control unit to control a multi-energy X-ray source to cause a multi-energy X-ray to be irradiated to a target during a predetermined time interval;
an X-ray detector to acquire a plurality of target images for each of at least two energy bands of the a multi-energy X-ray passing through the target where a contrast agent is applied; and
an image processing and analyzing unit to perform an image signal processing on the plurality of target images, including:
estimating respective initial images for at least one of plural materials, over the predetermined time interval, using the plurality of target images;
updating an initial estimated image of the estimated respective initial images based on, at least, one of later estimated images of the estimated respective initial images for the at least one of plural materials; and
generating a material decomposition image based on the updating of the initial estimated image,
with the image signal processing including at least one of:
processing the estimated respective initial images for the at least one of the plural materials, using the plurality of target images, for plural predetermined times within the predetermined time interval, and for each of the at least two energy bands of the multi-energy X-ray, performing a dynamics analysis of a measured amount of the contrast agent within the predetermined time interval, and measuring the amount of the contrast agent applied to the target by analyzing a material decomposition image from the target images for the at least one of plural materials, which include the contrast agent.

24. The apparatus of claim 23, wherein the image processing and analyzing unit further comprises:
a pre-processing unit to perform a pre-processing including at least one of: searching a predetermined Region of Interest (ROI) within the plurality of target images for a target image and separately storing the target image including the searched ROI from target images not including the searched ROI; and removing from at least one target image a motion artifact.

25. The apparatus of claim 23, wherein the image processing and analyzing unit further decomposes information from the plurality of target images into separately displayable components or materials including at least one of an image representing photoelectric attenuation of a corresponding area of the body including the target, an image representing a Compton scatter of the area, an image representing a subtraction image for at least the predetermined time interval corresponding to respective target images of the at least two energy bands, and an image representing an X-ray angiography for the area.

26. The apparatus of claim 23, wherein the image processing and analyzing unit further compares the measured dynamics with a dynamics table to diagnose whether a lesion or mass within the target is malignant.

* * * * *

UNITED STATES PATENT AND TRADEMARK OFFICE
CERTIFICATE OF CORRECTION

PATENT NO. : 8,761,485 B2
APPLICATION NO. : 12/929173
DATED : June 24, 2014
INVENTOR(S) : Kwang Eun Jang et al.

It is certified that error appears in the above-identified patent and that said Letters Patent is hereby corrected as shown below:

In the Claims

Column 14, Line 10 (Approx.), In Claim 23, after "of the" delete "a".

Signed and Sealed this
Fourth Day of November, 2014

Michelle K. Lee
*Deputy Director of the United States Patent and Trademark Office*